(12) United States Patent
Kobayashi et al.

(10) Patent No.: US 11,896,409 B2
(45) Date of Patent: Feb. 13, 2024

(54) X-RAY DIAGNOSIS APPARATUS

(71) Applicant: CANON MEDICAL SYSTEMS CORPORATION, Otawara (JP)

(72) Inventors: Yoshimasa Kobayashi, Nasushiobara (JP); Takehito Tomaru, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 17/360,239

(22) Filed: Jun. 28, 2021

(65) Prior Publication Data

US 2021/0401385 A1    Dec. 30, 2021

(30) Foreign Application Priority Data

Jun. 29, 2020   (JP) ................................ 2020-111980

(51) Int. Cl.
*A61B 6/00* (2006.01)
*A61B 6/02* (2006.01)

(52) U.S. Cl.
CPC ............ *A61B 6/4035* (2013.01); *A61B 6/025* (2013.01); *A61B 6/4021* (2013.01); *A61B 6/502* (2013.01)

(58) Field of Classification Search
CPC ...................................................... A61B 6/025
See application file for complete search history.

(56) References Cited

U.S. PATENT DOCUMENTS

| 2020/0100745 A1* | 4/2020 | Sato ..................... A61B 6/488 |
| 2020/0305809 A1* | 10/2020 | Schwoebel ........... H01J 35/147 |
| 2021/0100516 A1* | 4/2021 | Huck .................... A61B 6/025 |

FOREIGN PATENT DOCUMENTS

| JP | 11-108857 A | 4/1999 |
| JP | 2008-012206 A | 1/2008 |
| JP | 2013-005854 A | 1/2013 |
| JP | 2015-144808 A | 8/2015 |

OTHER PUBLICATIONS

Sprenger et al., "Distributed source x-ray technology for tomosynthesis imaging" NIH Public Access, ProcSPIE. Jan. 1, 2010; 7622: 76225M. do1: 10.1117/12.844586. pp. 1-16.

Office Action dated Nov. 28, 2023 in corresponding Japanese Patent Application No. 2020-111980, along with a machine-translation.

* cited by examiner

*Primary Examiner* — Dani Fox
(74) *Attorney, Agent, or Firm* — Oblon, McClelland, Maier & Neustadt, L.L.P.

(57) ABSTRACT

An X-ray diagnosis apparatus according to the embodiment disclosed herein includes an X-ray tube configured to have a plurality of focal points and configured to emit X-rays from each focal point, a radiation quality filter configured to change radiation quality of the X-rays emitted from each of the focal points, and a mover configured to move the radiation quality filter in a direction along which the focal points are aligned.

14 Claims, 10 Drawing Sheets

| FOCAL POINT NUMBER | ELAPSED TIME (SECONDS) |
|---|---|
| #1 | 2 |
| #2 | 4 |
| #3 | 6 |
| #4 | 8 |
| #5 | 10 |

X-RAY DIAGNOSIS APPARATUS

CROSS REFERENCE TO RELATED APPLICATIONS

This application is based upon and claims the benefit of priority from the prior Japanese Patent Application No. 2020-111980, filed on Jun. 29, 2020, the entire contents of which are incorporated herein by reference.

FIELD

Embodiments described herein and illustrated in the accompanying drawings relate to an X-ray diagnosis apparatus.

BACKGROUND

An imaging method is widely known, in which tomosynthesis imaging performed in mammography screening is used in an X-ray diagnosis. In the method, a single X-ray tube is moved to take a tomosynthesis image. However, since the X-ray tube has to be continuously moved to acquire image data, the movement of the focal point of the X-ray tube may cause a blur in the image.

In order to deal with this problem, several imaging methods have been developed, in which a fixed X-ray tube with multiple focal points is used so that an image may be taken without continuously moving the X-ray tube. Since the X-ray imaging is performed using X-rays emitted from the fixed X-ray tube, the occurrence of image blurring may be prevented.

However, a radiation quality filter for adjusting photon energy is needed for an X-ray tube having multiple focal points in order to change the radiation quality of X-rays, like conventional X-ray tubes. Such a radiation quality filter needs to have a wide area to cover all of the focal points since X-rays are emitted from all of the focal points. However, the radiation quality filter is formed of an expensive material such as molybdenum, rhodium, or silver. Therefore, an increase in the area of the radiation quality filter leads to an increase in the costs for manufacturing the X-ray diagnosis apparatus.

DETAILED DESCRIPTION

Embodiments of the X-ray diagnosis apparatus will now be described with reference to the accompanying drawings. In the following descriptions, elements having substantially the same structure and functions have the same numerical symbol, and the explanation of such elements is repeated only when it is necessary to do so.

First Embodiment

Figure 1:
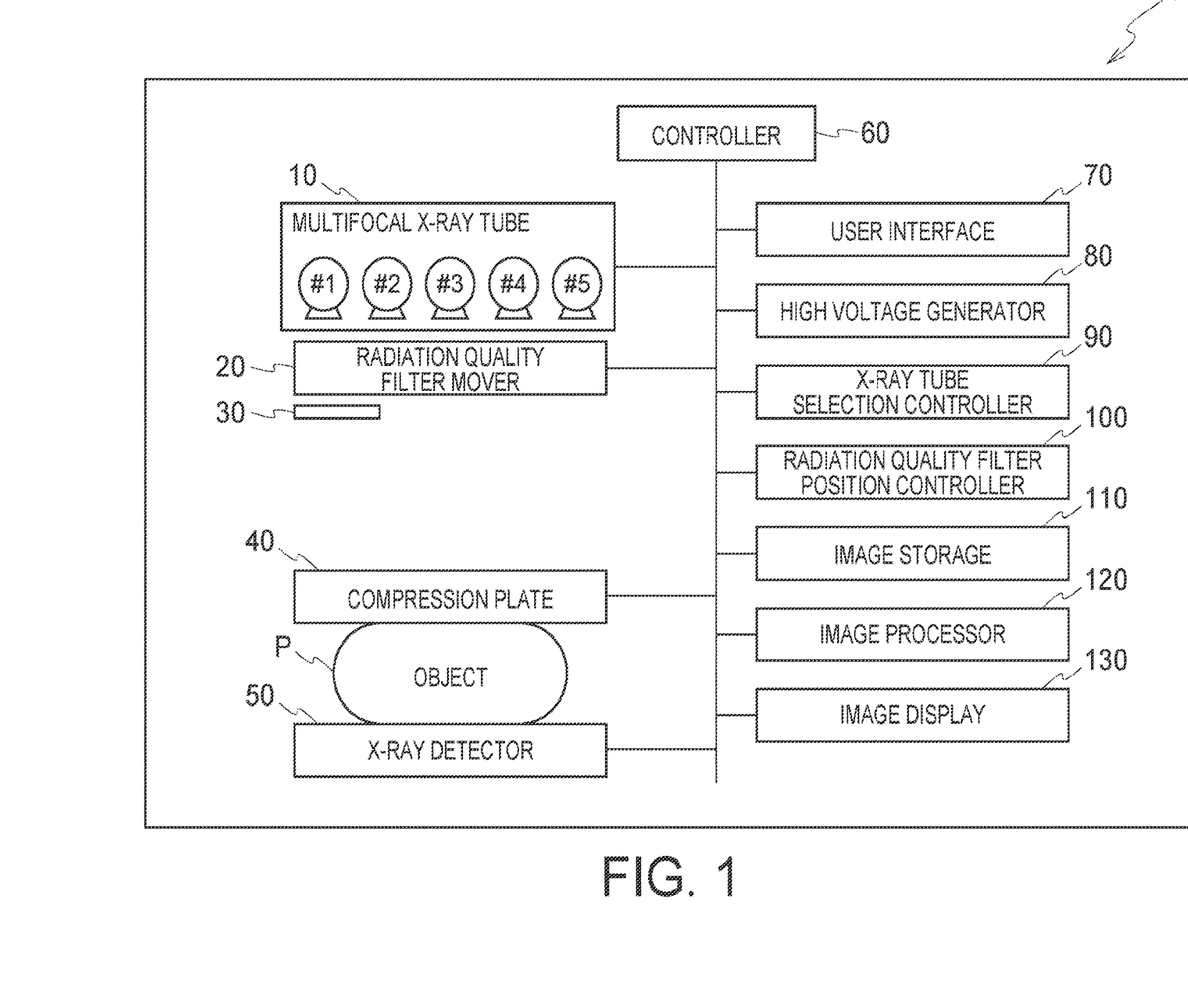
FIG. 1 is a block diagram illustrating the configuration of an X-ray diagnosis apparatus according to a first embodiment.

The configuration of an X-ray diagnosis apparatus 1 according to a first embodiment will first be described with reference to FIG. 1. As shown in FIG. 1, the X-ray diagnosis apparatus 1 is capable of performing X-ray imaging of an object P, and includes a multifocal X-ray tube 10, a radiation quality filter mover 20, a radiation quality filter 30, a compression plate 40, an X-ray detector 50, a controller 60, a user interface 70, a high voltage generator 80, an X-ray tube selection controller 90, a radiation quality filter position controller 100, an image storage 110, an image processor 120, and an image display 130.

The multifocal X-ray tube 10 has a plurality of focal points. X-rays are emitted from each of the focal points. The multifocal X-ray tube will be briefly described below. Examples of apparatuses that use X-rays to take X-ray images include an apparatus for performing tomosynthesis imaging in mammography screening, and an apparatus for taking long images to perform X-ray imaging over a wide and long region. Such X-ray imaging apparatuses take an X-ray image of a region necessary for the diagnosis by moving an X-ray tube. However, the X-ray image may have blurs, and it takes some time to obtain the X-ray image since the X-ray tube has to be moved. On the other hand, the X-ray tube having multiple focal points is capable of emitting X-rays independently from each focal point, and therefore taking a tomosynthesis image or a long image without moving the X-ray tube.

Like ordinary X-ray tubes having a single focal point, the multifocal X-ray tube 10 includes a filament serving as a cathode and a metal target serving as an anode within a vacuum envelope. The high voltage generator 80 supplies a tube voltage and a current corresponding to a tube current to the multifocal X-ray tube 10. The tube voltage is an acceleration voltage for accelerating an electron beam within the multifocal X-ray tube 10. A higher value of the tube voltage leads to a higher X-ray transmittance. The value of the tube current corresponds to the current value of the electron beam emitted from the filament.

The filament is formed of a carbon nanotube, for example, and generates thermoelectrons when the current corresponding to the tube current is supplied from the high voltage generator 80. Thus, the number of thermoelectrons generated in a unit time corresponds to the value of the tube current. The metal target is formed of tungsten, for example. The tube voltage supplied from the high voltage generator 80 is applied between the cathode and the anode to generate an electric field between the cathode and the anode. The thermoelectrons accelerated by the electric field collide with the metal target at the anode. As the result of the collision of the thermoelectrons with the metal target, X-rays are produced. As the tube voltage increases, the wavelength peak of the X-rays shifts toward the short wavelength side, and the energy of the X-rays also increases.

For example, the multifocal X-ray tube 10 in the first embodiment includes a plurality of cathodes in order to have a plurality of focal points. When the tube current is supplied to any one of the cathodes, thermoelectrons are emitted from one cathode to which the tube current is supplied. The thermoelectrons collide with the metal target at the anode to produce X-rays. The focal point for producing the X-rays may be selected by suitably selecting the cathode to which the tube current is supplied.

Alternatively, in order to have a plurality of focal points, the multifocal X-ray tube 10 may change the path of the thermoelectrons emitted from the cathode by using a deflector before the thermoelectrons collide with the metal target at the anode and produce the X-rays. The deflector changes the path of the thermoelectrons by changing the electric field or the magnetic field the deflector generates. When such a configuration is employed, only a single pair of cathode and anode is needed, like a common X-ray tube having a single focal point. The position of the focal point for emitting X-rays may be selected by controlling the intensity and the orientation of the electric field and/or the magnetic field generated by the deflector.

The multifocal X-ray tube 10 shown in FIG. 1 has five focal points #1 to #5. The focal point #1, the focal point #2, . . . , and the focal point #5 are sequentially arranged from the left to the right as shown in FIG. 1. The number of focal points in the multifocal X-ray tube 10 is not limited to five, but may be less than five or more than five depending on the objective and the characteristics of the X-ray diagnosis apparatus 1. Although the focal points are linearly arranged in FIG. 1, they are not necessarily arranged linearly but may be arranged along an arc or a curved line. Thus, the number of focal points and the arrangement of the focal points in the multifocal X-ray tube are not particularly limited.

The radiation quality filter mover 20 moves the radiation quality filter 30 along the direction in which the focal points are arranged in the multifocal X-ray tube 10. The multifocal radiation quality filter mover 20 is configured to move the radiation quality filter 30 to filter positions each corresponding to one of the focal points in the X-ray tube 10. In other words, the radiation quality filter mover 20 is configured to move the radiation quality filter 30 to the filter positions, each of which crosses the X-rays emitted from one of the multiple focal points. In this embodiment, for example, the multifocal X-ray tube 10 emits the X-rays downwards and the radiation quality filter mover 20 is located under the multifocal X-ray tube 10.

Figure 2:
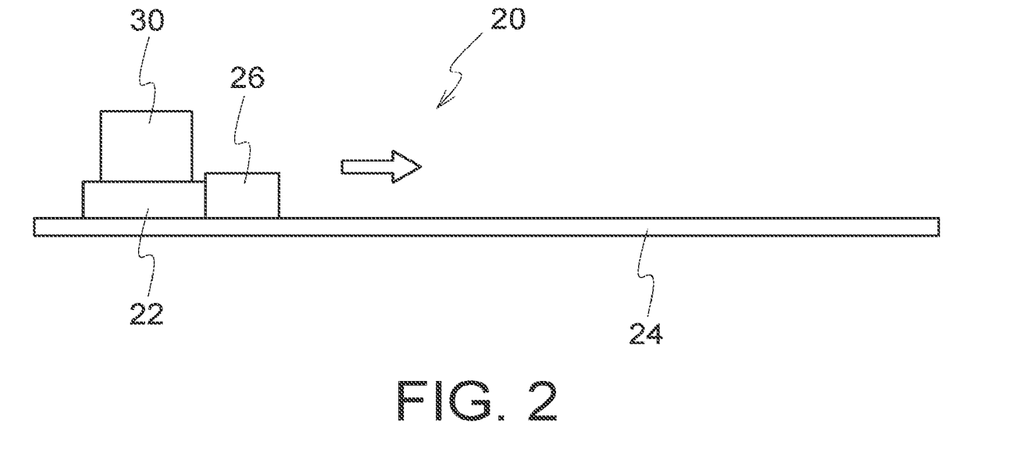
FIG. 2 is a block diagram illustrating an example of the configuration of a radiation quality filter mover included in the X-ray diagnosis apparatus shown in FIG. 1.

FIG. 2 is a block diagram illustrating an example of the configuration of the radiation quality filter mover 20 according to the first embodiment. As shown in FIG. 2, the radiation quality filter mover 20 includes, for example, a support 22 that supports the radiation quality filter 30, a rail 24 extending in the direction along which the focal points of the multifocal X-ray tube 10 are arranged, the rail 24 being used for moving the support 22 on which the radiation quality filter 30 is placed, and a driving mechanism 26 such as a motor that supplies moving power to the support 22.

The rail 24 extends in the direction in which the focal points of the multifocal X-ray tube 10 are arranged. In other words, the rail 24 is placed such that the radiation quality filter mover 20 may move on the rail 24 to move the radiation quality filter 30 to each filter position corresponding to one of the focal points. The number of the rail 24 may be one, two or more.

For example, if the focal points of the multifocal X-ray tube 10 are linearly arranged, the rail 24 is linearly placed along the focal points. If the focal points of the multifocal X-ray tube 10 are arranged along an arc, the rail 24 is placed along an arc arrangement of the focal points. The rail 24 of the present embodiment is one of examples as a guider which guides the support 22 on which the radiation quality filter 30 is mounted. The guider may be constructed as, for example, a groove for guiding the support 22, a guiding device using a magnetic power, or the like.

The driving mechanism 26 includes, for example, interface circuitry for sending a signal to and receiving a signal from a component of the X-ray diagnosis apparatus 1 other than the radiation quality filter mover 20 such as the radiation quality filter position controller 100, and a control circuit for controlling the movement of the radiation quality filter mover 20. The driving mechanism 26 may be constructed as, for example, an electrical rotational motor, an electrical liner motor, an engine or the like. Moreover, the driving mechanism 26 may be constructed as, for example, a moving own weight device which moves the radiation quality filter 30 downwardly on a slope form a top to a bottom and stops the radiation quality filter 30 at a predetermined position.

Since the multifocal X-ray tube 10 in the first embodiment has the five focal points #1 to #5, the radiation quality filter mover 20 moves in a direction indicated by the arrow in FIG. 2, for example, to move the radiation quality filter 30 to five filter positions corresponding to the focal points from which the X-rays are emitted. The radiation quality filter mover 20 is capable of moving in the direction opposite to the direction indicated by the arrow in FIG. 2. However, when X-rays are emitted from the focal points of the multifocal X-ray tube 10, the radiation quality filter mover 20 moves in one direction so that the X-rays are sequentially emitted from the focal point #1 to the focal point #5 in this order.

Referring back to FIG. 1, the radiation quality filter 30 is provided to the support 22 of the radiation quality filter mover 20 shown in FIG. 2. The radiation quality filter 30 is used to adjust the energy of photons, i.e., the intensity of X-rays, by changing the radiation quality of the X-rays emitted from the multifocal X-ray tube 10 in the same manner as the radiation quality filters of ordinary single-focal point X-ray tubes. Also, the presence of the radiation quality filter 30 may reduce the dosage received by the object P. Such materials as molybdenum (Mo), rhodium (Rh), and silver (Ag) are used to manufacture the radiation quality filter 30.

When an X-ray image is taken by using a multifocal X-ray tube, X-rays are emitted from each of the multiple focal points on a one-by-by basis. Therefore, the radiation quality filter 30 needs to have only an area that corresponds to an irradiation field of X-rays from a single focal point. In more detail, the radiation quality filter 30 according to the first embodiment needs to have an area sufficient to operate as a filter for X-rays emitted from a single focal point, but does not necessarily have an area to cover X-rays from the other focal points since the X-rays are not emitted from more than one focal point.

The area of the radiation quality filter 30 is therefore determined by the irradiation field irradiated with X-rays from each focal point based on such conditions as the beam diameter of the X-rays emitted from each focal point of the multifocal X-ray tube 10, and the distance between the multifocal X-ray tube 10 and the radiation quality filter 30. Furthermore, the radiation quality filter 30 needs to have a uniform thickness and density as much as possible since the radiation quality of the X-rays from each focal point needs to be the same after the X-rays pass through the radiation quality filter 30 in order to reduce the unevenness in the X-ray image.

The compression plate 40 is placed above the X-ray detector 50, in the direction of the multifocal X-ray tube 10 from the detector 50. The compression plate 40 is used to compress and fix the breast, which is the object P, placed on the X-ray detector 50 for the X-ray imaging, for example. In order to do so, the compression plate 40 has a mechanism to vertically move. Since the compression plate 40 is placed above the object P, it is formed of a material that transmits X-rays, such as a transparent acrylic plate, also in consideration of the visibility.

Although the X-ray diagnosis apparatus 1 is an apparatus for taking a tomosynthesis image in mammography screening in the example shown in FIG. 1, the compression plate 40 is not always necessary if the X-ray diagnosis apparatus 1 is of a different type. For example, the compression plate 40 is not necessary if the X-ray diagnosis apparatus 1 performs X-ray imaging of something other than breasts, such as X-ray imaging of chest.

The object P is placed on the X-ray detector 50, which detects a penetrated X-ray of the X-rays emitted from the multifocal X-ray tube 10 and passing through the object P in the units of pixels, and outputs an image signal that is corresponding to the detected X-ray dose to the image processor 120. The X-ray detector 50 may be, for example, a flat panel detector (FPD) that detects X-rays received by a detection surface.

The controller 60 performs the overall control of the X-ray diagnosis apparatus 1 according to the first embodiment. Specifically, the controller 60 sends a necessary command to each component of the X-ray diagnosis apparatus 1 in order to execute a command inputted by the user through the user interface 70. The controller 60 includes, for example, a storage medium that stores a program necessary for performing an inspection by means of the X-ray diagnosis apparatus 1, and a processor for executing the program.

The user interface 70 has a mechanism for enabling the user to perform an operation required for taking an X-ray image of the object P using the X-ray diagnosis apparatus 1. For example, if the user interface 70 has an exposure switch, the user may press down the exposure switch to send a command to initiate the X-ray imaging by emitting X-rays from the multifocal X-ray tube 10. If the user interface 70 has a touch panel, the user may touch the touch panel, as the necessity arises, to input a command necessary for the X-ray diagnosis to the X-ray diagnosis apparatus 1. In the first embodiment, the user interface 70 may include arbitrary input means other than the exposure switch or the touch panel, such as a display, a switch button, a keyboard, a mouse device, and a trackball.

The high voltage generator 80 supplies the tube voltage and the current corresponding to the tube current to the multifocal X-ray tube 10, and includes, for example, a transformer and a rectifier. The transformer raises an alternating current supplied from an AC power supply in accordance with the required tube voltage, and supplies the raised AC voltage to the rectifier. The rectifier rectifies the AC voltage supplied from the transformer, and outputs a pulsating voltage as the tube voltage, which has only a positive component.

The X-ray tube selection controller 90 performs a control operation in which a focal point from which the X-rays are to be emitted (for example, the focal point #1 shown in FIG. 1) is selected from the multiple focal points of the multifocal X-ray tube 10, and the tube voltage set by the high voltage generator 80 is applied to the selected focal point. The X-ray tube selection controller 90 also transmits a signal including information such as the selected focal point to the radiation quality filter position controller 100.

The radiation quality filter position controller 100 sends a command to the radiation quality filter mover 20 to move the radiation quality filter 30 to the filter position corresponding to the selected focal point (for example, the focal point #1 shown in FIG. 1) selected by the X-ray tube selection controller 90. For example, if the X-rays are emitted from the focal point #1, the radiation quality filter position controller 100 controls the radiation quality filter mover 20 to move the radiation quality filter 30 to a filter position corresponding to the focal point #1. If the X-rays are emitted from the focal point #2 next, the radiation quality filter position controller 100 controls the radiation quality filter mover 20 to move the radiation quality filter 30 from the filter position corresponding to the focal point #1 to the filter position corresponding to the focal point #2. In the first embodiment, the radiation quality filter position controller 100 and the controller 60 constitute a controller that controls the radiation quality filter mover 20.

The X-ray diagnosis apparatus 1 according to the first embodiment is intended to reduce the manufacturing costs by reducing the area of the radiation quality filter 30 that changes the radiation quality of the X-rays from each of the focal points of the multifocal X-ray tube 10. In other words, the radiation quality filter 30 according to the first embodiment does not have an area covering the entire area irradiated with the X-rays from all of the focal points. Therefore, the radiation quality filter position controller 100 performs the position control to move the radiation quality filter 30 to the filter position corresponding to the focal point from which the X-rays are emitted. The radiation quality filter position controller 100 outputs a command or information to the radiation quality filter mover 20 required for physically moving the radiation quality filter 30.

In order to determine the position to which the radiation quality filter mover 20 should be moved, the radiation quality filter position controller 100 and/or the controller 60 according to the first embodiment may include, for example, a moving position table in which each of the focal points of the multifocal X-ray tube 10 is associated with a position of the radiation quality filter mover 20. The radiation quality filter position controller 100 determines the irradiation field to which the X-rays are emitted from each of the focal points based on the moving position table, and moves the radiation quality filter mover 20 to move the radiation quality filter 30 to the filter position corresponding to the focal point from which the X-rays are emitted.

The image storage 110 stores an image (X-ray image) formed by emitting the X-rays from each of the focal points of the multifocal X-ray tube 10 and passing through the object P. Since a tomosynthesis image is to be formed in the first embodiment, a series of X-ray images having been subjected to image processing performed by the image processor 120 are stored in the image storage 110. The image storage 110 includes, for example, storage circuitry. The storage circuitry includes, for example, a magnetic or optical storage medium, or a readable storage medium such as a semiconductor memory.

The image processor 120 generates an X-ray image based on the X-ray image signal outputted from the X-ray detector 50. The image processor 120 includes, for example, analog-to-digital conversion circuitry and an image corrector. The analog-to-digital conversion circuitry converts the X-ray image signal outputted from the X-ray detector 50, which is an analog signal, to a digital image signal. The image corrector performs necessary correction processing on the digital image signal outputted from the analog-to-digital conversion circuitry to generate a corrected X-ray image. The correction processing for the digital image is performed on each of the pixels in the X-ray detector 50. The generated X-ray image is stored in the image storage 110 or displayed on the image display 130, for example. The analog-to-digital conversion circuitry may be included in the X-ray detector 50. In this case, the image processor 120 acquires the digital image signal from the X-ray detector 50.

The X-ray diagnosis apparatus 1 according to the first embodiment performs image reconstruction processing on a plurality of X-ray images taken for a single object P in order to perform the X-ray imaging according to a tomosynthesis imaging method. The X-ray images taken by using the multiple focal points in the multifocal X-ray tube 10 are read from the image storage 110 and reconstructed to produce a single X-ray image.

The image processor 120 includes, for example, storage circuitry and processing circuitry. In the same manner as the description above, the storage circuitry includes a magnetic or optical storage medium or a readable storage medium such as a semiconductor memory. The storage circuitry also stores various processing functions performed by the processing circuitry in the form of programs that may be executed by a computer. The processing circuitry is, for example, a processor which executes a program read from the storage circuitry to perform a processing function corresponding to each of the programs. Examples of the image processing performed by the image processor 120 includes image reconstruction processing related to, for example, Filtered Back Projection, ML-EM, or OS-EM, and image adjustment processing such as gradation processing, frequency processing, and dynamic range compression.

The image display 130 displays an X-ray image having been subjected to the image processing performed by the image processor 120. For example, the image display 130 may be a liquid crystal display device or a cathode ray tube (CRT) display for showing the X-ray image to the user. There is no particular limitation on the method for displaying the X-ray image.

The foregoing are the descriptions of the X-ray diagnosis apparatus 1 according to the first embodiment. A process of X-ray imaging performed by the X-ray diagnosis apparatus 1 according to the first embodiment will then be described below.

Figure 3:
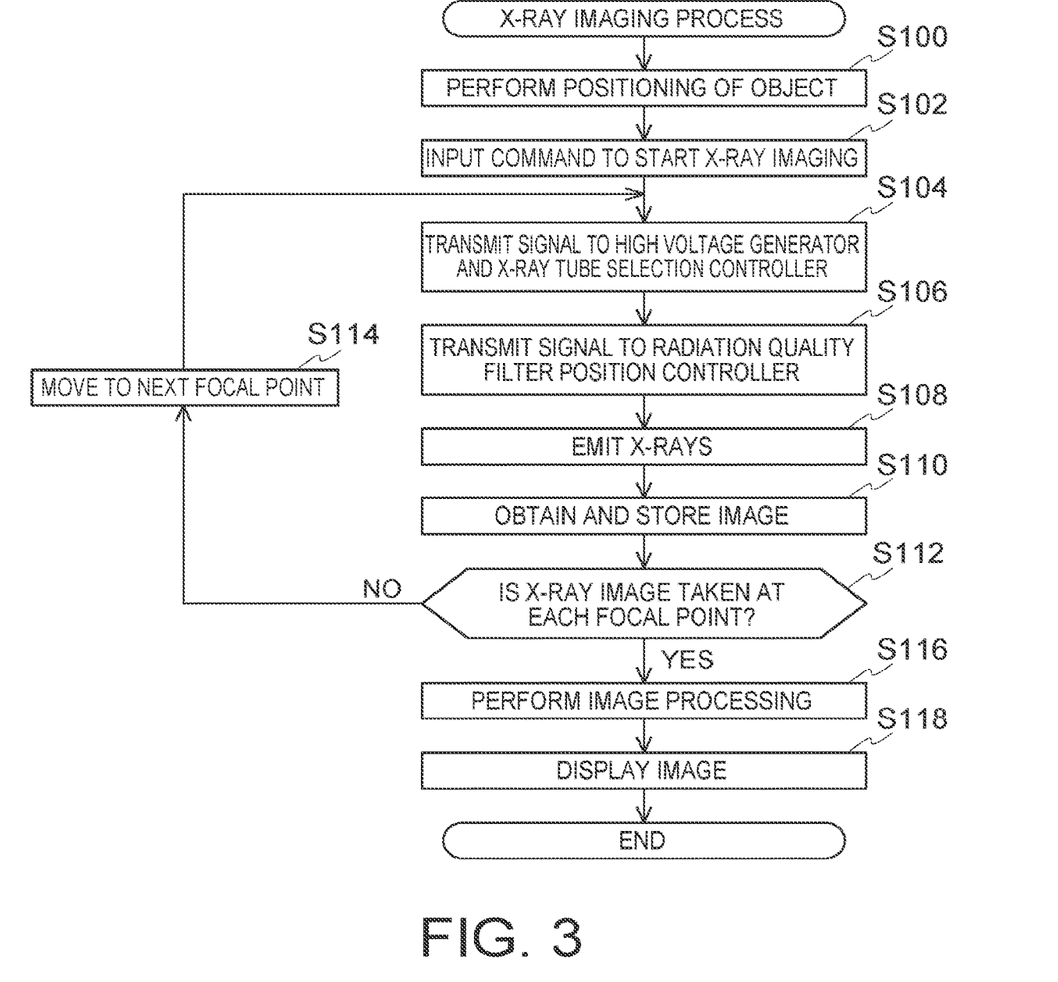
FIG. 3 is a flowchart of an X-ray imaging process performed by the X-ray diagnosis apparatus according to the first embodiment.

FIG. 3 is a flowchart showing sequential steps of the X-ray imaging in the first embodiment. The X-ray imaging is performed during a mammography screening. A plurality of X-ray images are taken for an object P based on the positioning of the object P, and reconstruction processing is performed on the taken X-ray images to perform an X-ray image diagnosis using a tomosynthesis imaging method.

The user performs the positioning of an object P for which the X-ray diagnosis is performed by using the X-ray diagnosis apparatus 1 (step S100). In the first embodiment, the object P is a breast, which is placed on the X-ray detector 50 and compressed and fixed at a position suitable for the X-ray diagnosis by the compression plate 40 as shown in FIG. 1.

The user then inputs a command to start the X-ray imaging via the user interface 70 (step S102). If the exposure switch is provided as the user interface 70, for example, the user may input the command to start the X-ray imaging by pressing down the exposure switch. Several operations required for the X-ray imaging are started by inputting the command.

The controller 60 then transmits a signal to the high voltage generator 80 and the X-ray tube selection controller 90 (step S104). Upon receiving the signal, the high voltage generator 80 generates the tube voltage, the tube current, and the filament current having predetermined values. The values of the tube voltage, the tube current, and the filament current are predetermined by the input through the user interface 70 performed by the user. Alternatively, the values of the tube voltage, the tube current, and the filament current may be calculated in advance based on such information as the type of test and the size of the object P inputted through the user interface 70 by the user. Upon receiving the signal, the X-ray tube selection controller 90 controls the multifocal X-ray tube 10 so that X-rays are emitted from the focal point selected by the signal. The multifocal X-ray tube 10 according to the first embodiment has the five focal points #1 to #5. The X-ray tube selection controller 90 controls the multifocal X-ray tube 10 so that the X-rays are first emitted from the focal point #1, for example.

At the same time as step S104, the controller 60 transmits a signal to the radiation quality filter position controller 100 (step S106). Upon receiving the signal, the radiation quality filter position controller 100 controls the radiation quality filter mover 20 to position the radiation quality filter 30 at a filter position corresponding to the focal point selected by the signal. For example, the radiation quality filter position controller 100 sends information on the position to which the radiation quality filter 30 is moved, i.e., the filter position information, to the radiation quality filter mover 20 based on the moving position table in which each focal point of the multifocal X-ray tube 10 is associated with a position of the radiation quality filter mover 20. Based on the received information on the filter position, the radiation quality filter mover 20 moves the radiation quality filter 30. For example, if the selected focal point is the focal point #1 as described above, the radiation quality filter position controller 100 controls the radiation quality filter mover 20 so that the radiation quality filter 30 stops at the filter position at which the radiation quality filter 30 crosses the X-rays emitted from the focal point #1 of the multifocal X-ray tube 10.

The controller 60 then causes the X-ray tube to emit X-rays from the focal point selected by the X-ray tube selection controller 90 (step S108). For example, if the selected focal point is the focal point #1 as described above, the tube voltage, the tube current, and the filament current each having a value set by the high voltage generator 80 are supplied to the focal point #1 selected by the X-ray tube selection controller 90 to emit the X-rays from the focal point #1 of the multifocal X-ray tube 10. At this time, the radiation quality filter 30 stays at the filter position for filtering the X-rays emitted from the focal point #1. When passing through the radiation quality filter 30, the X-rays emitted from the focal point #1 of the multifocal X-ray tube 10 change in radiation quality to have an X-ray spectrum suitable for performing the X-ray imaging on the object P. The X-rays then pass through the compression plate 40 and the object P, and reach the X-ray detector 50.

The controller 60 then sends X-ray image signals in the unit of pixel to the image processor 120 based on the X-rays passing through the compression plate 40 and the object P and detected by the X-ray detector 50, to generate a single X-ray image (step S110). The generated X-ray image is stored in the image storage 110. The X-ray imaging for generating a single X-ray image relating to one focal point is completed. If the focal point that is first selected is the focal point #1, the X-ray imaging using the X-rays emitted from the focal point #1 of the multifocal X-ray tube 10 is completed.

The controller 60 then determines whether an X-ray image is formed by using each of the focal points of the multifocal X-ray tube 10 (step S112). The multifocal X-ray tube 10 according to the first embodiment has the five focal points #1 to #5. Therefore, if the X-ray imaging is started from the focal point #1, for example, the X-ray imaging sequentially proceeds to the focal point #2, the focal point #3, the focal point #4, and the focal point #5. At step S112, the controller 60 determines whether an X-ray image is formed by using each of the five focal points.

If the X-ray imaging has not been performed by using all of the focal points (No at step S112), the controller 60 changes the focal point from which the X-rays are emitted to a next focal point (step S114), and repeats the process from step S104 described above. Then, the X-ray imaging is performed by using the next focal point.

If it is determined that the X-ray imaging has been performed by using all of the focal points (Yes at S112), the controller 60 performs image processing based on the X-ray images formed by the X-rays emitted from the focal points of the multifocal X-ray tube 10 (step S116). In the image processing, the image processor 120 included in the X-ray diagnosis apparatus 1 reads the X-ray images stored in the image storage 110, and performs image regenerating processing and image adjustment processing to produce a single X-ray image based on the X-ray images.

The controller 60 then causes the image display 130 to display the X-ray image having been subjected to the image processing at step S116 so that the user may perform the X-ray diagnosis of the object P (step S118). The X-ray image produced at step S116 may be stored in the image storage 110 if necessary. The X-ray imaging process is completed at step S118.

As described above, when an X-ray image is taken by using the multifocal X-ray tube 10 included in the X-ray diagnosis apparatus 1 according to the first embodiment, the radiation quality filter 30 having an area corresponding to the area irradiated with the X-rays emitted from each focal point is moved by the radiation quality filter mover 20 to a filter position corresponding to the focal point from which the X-rays are emitted, the focal point being selected from a plurality of focal points. Therefore, the area of the radiation quality filter 30 may be reduced, thereby reducing the manufacturing costs of the radiation quality filter 30. In other words, since it is not necessary to prepare a radiation quality filter having an area that covers all of the focal points, the amount of the expensive material required to manufacture the radiation quality filter may be reduced.

Second Embodiment

In the first embodiment described above, the radiation quality filter mover 20 stops at each of the filter positions, and the X-rays are emitted from the multifocal X-ray tube 10 while the radiation quality filter 30 is not moving. In a second embodiment, the X-rays are emitted from the multifocal X-ray tube 10 while the radiation quality filter mover 20 is moving, and therefore the radiation quality filter 30 is moving. This is a difference between the second embodiment and the first embodiment. The difference will be described below.

Figure 4:
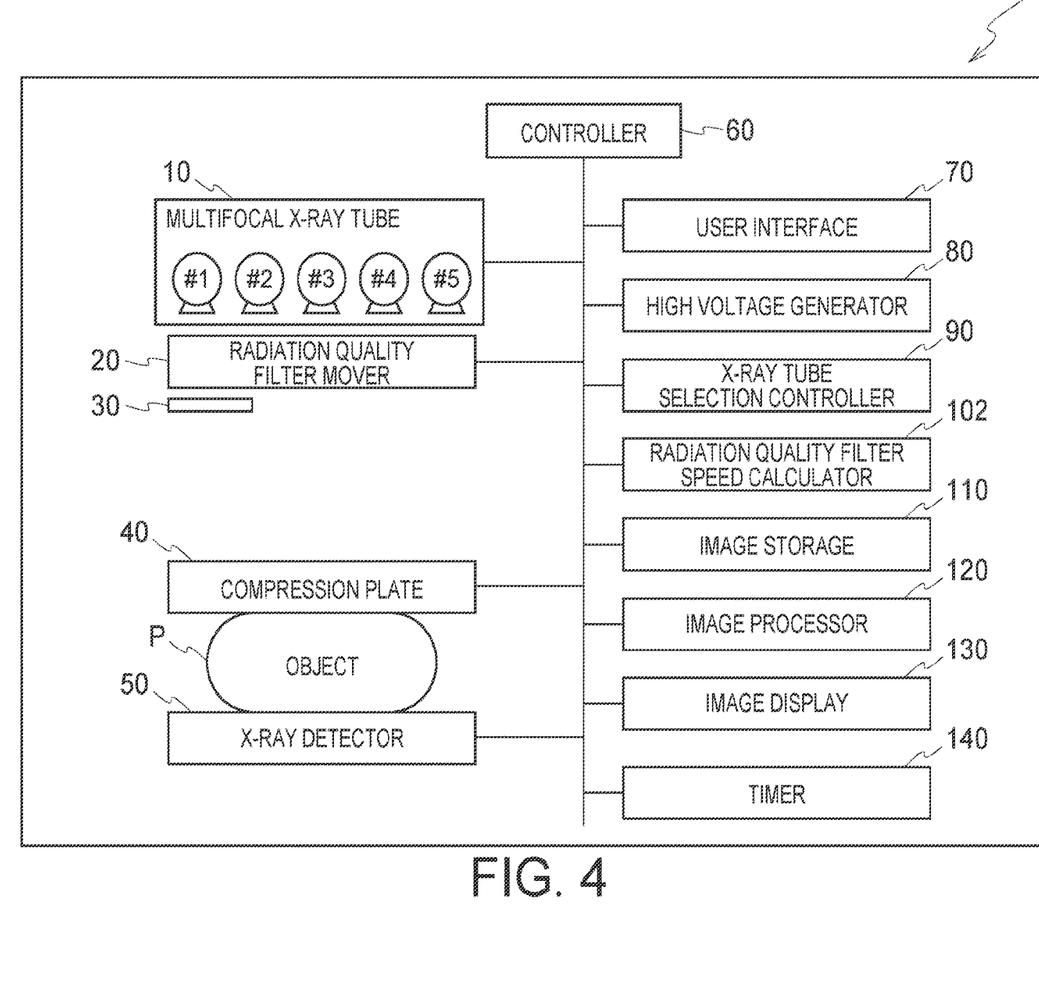
FIG. 4 is a block diagram illustrating the configuration of an X-ray diagnosis apparatus according to a second embodiment.

FIG. 4 is a block diagram for explaining the configuration of the X-ray diagnosis apparatus 1 according to the second embodiment. As shown in FIG. 4, the X-ray diagnosis apparatus 1 is capable of performing X-ray imaging of the object P, like the first embodiment described above. The difference between the second embodiment and the first embodiment lies in that a radiation quality filter speed calculator 102 is provided instead of the radiation quality filter position controller 100, and a timer 140 is added.

The radiation quality filter speed calculator 102 calculates the speed at which the radiation quality filter mover 20 moves the radiation quality filter 30. In the second embodiment, the radiation quality filter mover 20 does not stop the radiation quality filter 30 when the X-rays are emitted from each focal point of the multifocal X-ray tube 10. That is, in order to emit the X-rays from each focal point of the multifocal X-ray tube 10 while the radiation quality filter 30 does not stop, the radiation quality filter 30 has to be positioned at the filter positions, each of which crosses the X-rays emitted from one of the multiple focal points. If the radiation quality filter 30 is not at the filter position, the radiation quality of the X-rays cannot be changed since the emitted X-rays do not pass through the radiation quality filter 30. Therefore, the radiation quality filter speed calculator 102 calculates the speed at which the radiation quality filter mover 20 moves the radiation quality filter 30 so that when X-rays are emitted from each focal point of the multifocal X-ray tube 10, the radiation quality filter 30 passes the filter position corresponding to the focal point. In the second embodiment, the radiation quality filter speed calculator 102 and the controller 60 constitute a controller for controlling the radiation quality filter mover 20.

The timer 140 provides time information required by the X-ray diagnosis apparatus 1 according to the second embodiment. The X-ray tube selection controller 90 performs a control operation based on the provided time information, so that the high voltage generator 80 applies the tube voltage and others to the multifocal X-ray tube 10 at a predetermined time, for example. The radiation quality filter speed calculator 102 calculates the moving speed of the radiation quality filter mover 20 based on the provided time information. In order for the radiation quality filter 30 to pass the filter position corresponding to the focal point of the multifocal X-ray tube 10 from which X-rays are emitted, the X-ray tube selection controller 90 that performs the X-ray radiation control and the radiation quality filter speed calculator 102 that performs the control of the radiation quality filter mover 20 need to operate in synchronization with each other. The timer 140 may be realized by using a stopwatch function or a watch function held by a computer that performs the control operation.

The foregoing is the explanation on the difference in configuration between the X-ray diagnosis apparatus 1 according to the second embodiment and the X-ray diagnosis apparatus 1 according to the first embodiment. A process relating to the X-ray imaging performed by the X-ray diagnosis apparatus 1 according to the second embodiment will be described below.

Figure 5:
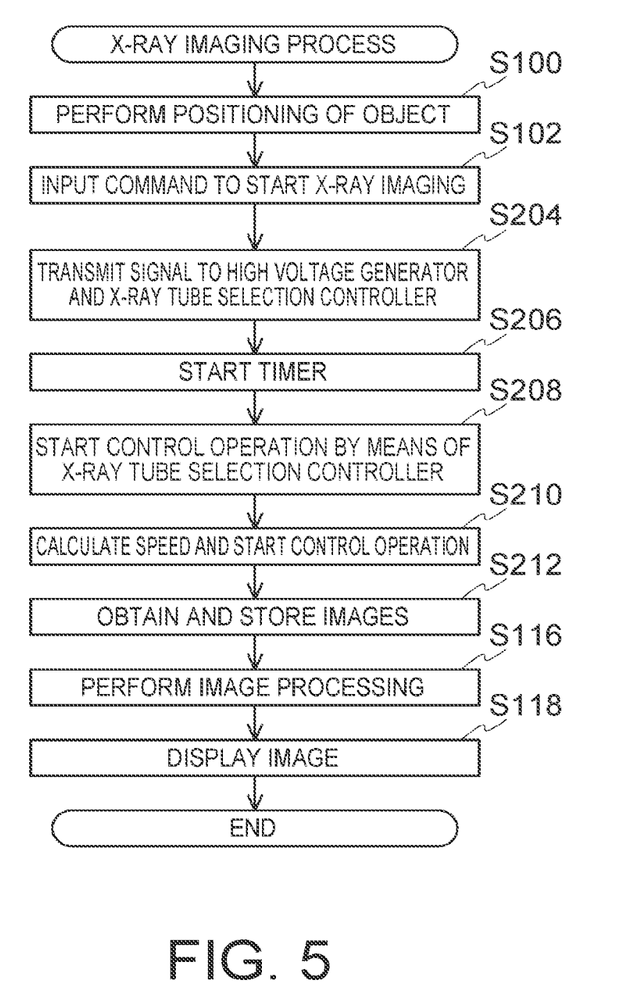
FIG. 5 is a flowchart of an X-ray imaging process performed by the X-ray diagnosis apparatus according to the second embodiment.

FIG. 5 is a flowchart of an X-ray imaging process according to the second embodiment. FIG. 5 corresponds to FIG. 3 illustrating the flowchart relating to the first embodiment.

The X-ray imaging process is the same as that of the first embodiment from the positioning of the object P (step S100) to the input by the user of a command to start X-ray imaging (step S102).

After step S102, the controller 60 transmits a signal to the high voltage generator 80 and the X-ray tube selection controller 90 (step S204). Upon receiving the signal, the high voltage generator 80 generates the tube voltage, the tube current, and the filament current having predetermined values. Upon receiving the signal, the X-ray tube selection controller 90 generates a radiation timetable which determines at which number of seconds after the start of measurement by the timer 140, X-rays are emitted from each focal point of the multifocal X-ray tube 10.

Figure 6:
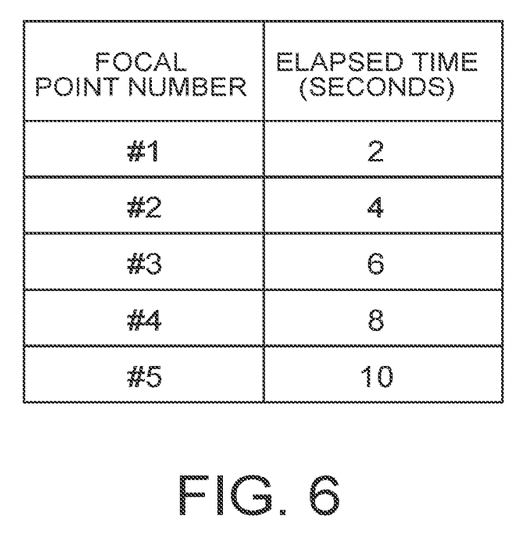
FIG. 6 is a diagram showing an example of a radiation timetable generated by an X-ray tube selection controller included in the X-ray diagnosis apparatus shown in FIG. 4.

FIG. 6 is a diagram showing an example of a radiation timetable generated by the X-ray tube selection controller 90 according to the second embodiment. As shown in FIG. 6, the radiation timetable according to the second embodiment stores the focal point numbers #1 to #5 each assigned to one of the focal points, and the elapsed time at which X-rays are emitted from each of the focal points. In other words, the radiation timetable determines the number of seconds measured by the timer 140 at which X-rays are emitted from each of the focal points.

Referring back to FIG. 5, the controller 60 transmits a signal to the timer 140 to start measuring time (step S206). At the same time, the X-ray tube selection controller 90 refers to the radiation timetable for the time measured by the timer 140. When the measured time matches the time on the radiation timetable, the X-ray tube selection controller 90 performs a control operation to apply the tube voltage, the tube current, and the filament current that are generated in advance by the high voltage generator 80 to the multifocal X-ray tube 10 (step S208).

Also at the same time, the controller 60 inputs the radiation timetable generated by the X-ray tube selection controller 90 to the radiation quality filter speed calculator 102. Using the inputted radiation timetable, the radiation quality filter speed calculator 102 calculates the speed of the radiation quality filter mover 20 to enable the radiation quality filter 30 to pass a filter position corresponding to a focal point of the multifocal X-ray tube 10 from which X-rays are emitted (step S210). The radiation quality filter speed calculator 102 controls the radiation quality filter mover 20 so that the radiation quality filter 30 moves at the calculated speed.

After the setting of the radiation quality filter mover 20, the high voltage generator 80, the X-ray tube selection controller 90, and the timer 140 is completed, X-rays are emitted in turn from the focal points to sequentially form X-ray images (step S212). Specifically, the X-ray tube selection controller 90 selects a focal point from which the X-rays are emitted at a designated elapsed time based on the time information from the timer 140 and the radiation timetable in which the number of seconds elapsed from the start time of the measurement by the timer 140 is associated with the number of the focal point from which X-rays are emitted. On the other hand, the radiation quality filter speed calculator 102 controls the radiation quality filter mover 20 to move the radiation quality filter 30 at the calculated speed to pass the filter position corresponding to the focal point from which the X-rays are emitted. For example, in the second embodiment, five X-ray images are sequentially taken at step S212 by using the X-rays emitted from the focal points #1 to #5. The taken X-ray images are stored in the image storage 110.

Next, image processing of the X-ray images taken by using the X-rays emitted from the focal points of the multifocal X-ray tube 10 is performed (step S116), and the result is displayed on the image display 130 (step S118). What are performed at step S116 and step S118 are the same as those in the first embodiment.

As described above, the X-ray diagnosis apparatus 1 according to the second embodiment is capable of sequentially taking a plurality of X-ray images of the object P without stopping the movement of the radiation quality filter 30. As a result, the manufacturing costs of the radiation quality filter 30 may be reduced, like the first embodiment, and time may be save since the radiation quality filter 30 does not stop. Therefore, the X-ray images may be taken more speedily.

Since the X-rays are emitted from each of the focal points of the multifocal X-ray tube 10 while the radiation quality filter 30 is moved, the X-rays passing through the radiation quality filter 30 is homogenized even if the density and/or the thickness of the material of the radiation quality filter 30 (for example, Rh or Ag) is not uniform. Therefore, blurs in the X-ray images may be reduced. Since it is not necessary to improve the uniformity of the radiation quality filter 30, the manufacturing costs of the radiation quality filter 30 may be reduced further.

Although the radiation quality filter mover 20 according to the second embodiment is intended to move at a constant speed calculated by the radiation quality filter speed calculator 102, the speed of the radiation quality filter mover 20 may be reduced at each filter position. Specifically, when the radiation quality filter mover 20 is about to reach the filter position corresponding to the focal point from which the X-rays are about to be emitted, the radiation quality filter mover 20 may not be stopped, but the speed of the radiation quality filter mover 20 may be reduced so that the timing at which X-rays are emitted from the focal point may match the timing the radiation quality filter mover 20 reach the filter position.

Third Embodiment

In the first embodiment and the second embodiment described above, the radiation quality filter mover 20 includes a single type of radiation quality filter 30. However, in a third embodiment, the radiation quality filter 30 includes a plurality of sub-radiation quality filters formed of different materials, so that the radiation quality of the X-rays may be changed in accordance with the characteristics of the object P, or a single imaging operation may produce X-ray images of the object P with X-rays having different radiation qualities. The differences between the third embodiment and the first embodiment described above will be described blow. The features of the third embodiment may also be used for the X-ray diagnosis apparatus 1 according to the second embodiment.

Figure 7:
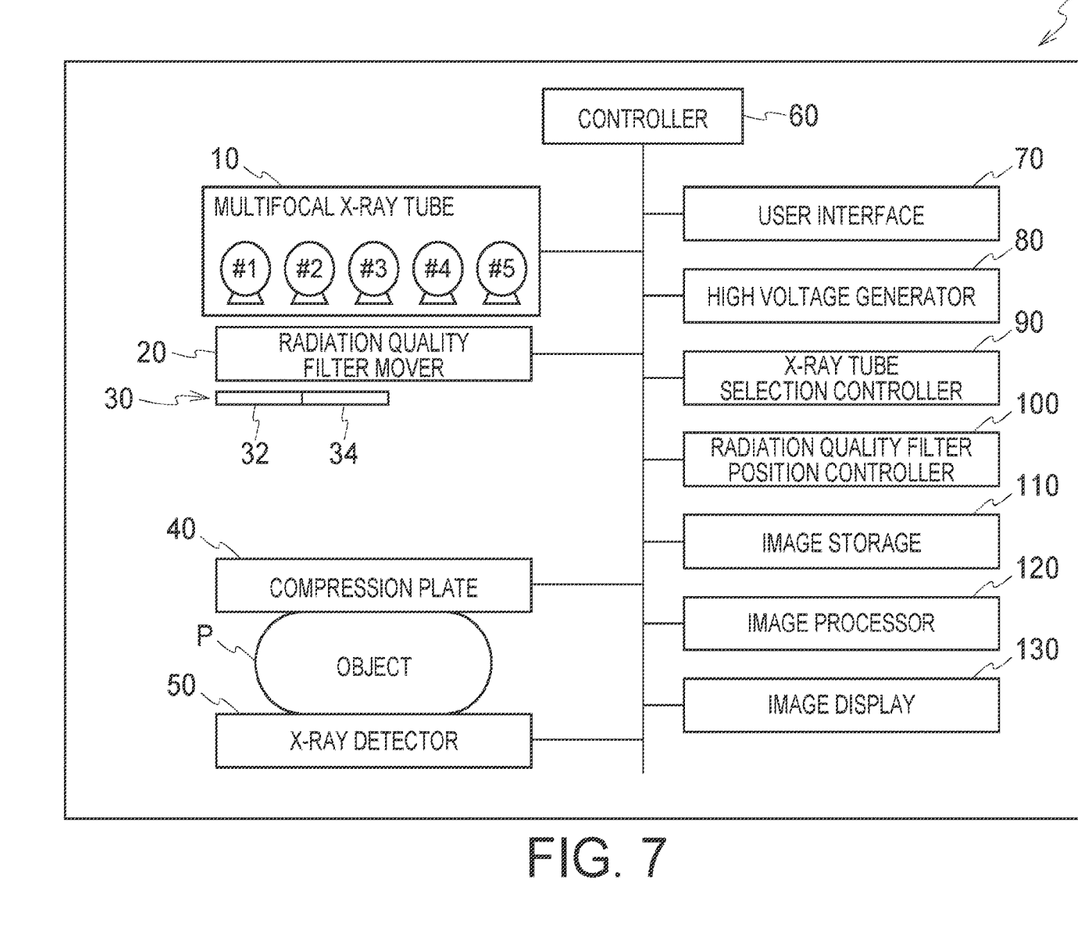
FIG. 7 is a block diagram illustrating the configuration of an X-ray diagnosis apparatus according to a third embodiment.

FIG. 7 is a block diagram illustrating the configuration of an X-ray diagnosis apparatus 1 according to the third embodiment. As shown in FIG. 7, the X-ray diagnosis apparatus 1 is capable of X-ray imaging of an object P, like that of the first embodiment described above. The difference between the third embodiment and the first embodiment lies in the fact that the radiation quality filter 30 includes two sub-radiation quality filters 32 and 34.

Figure 8:
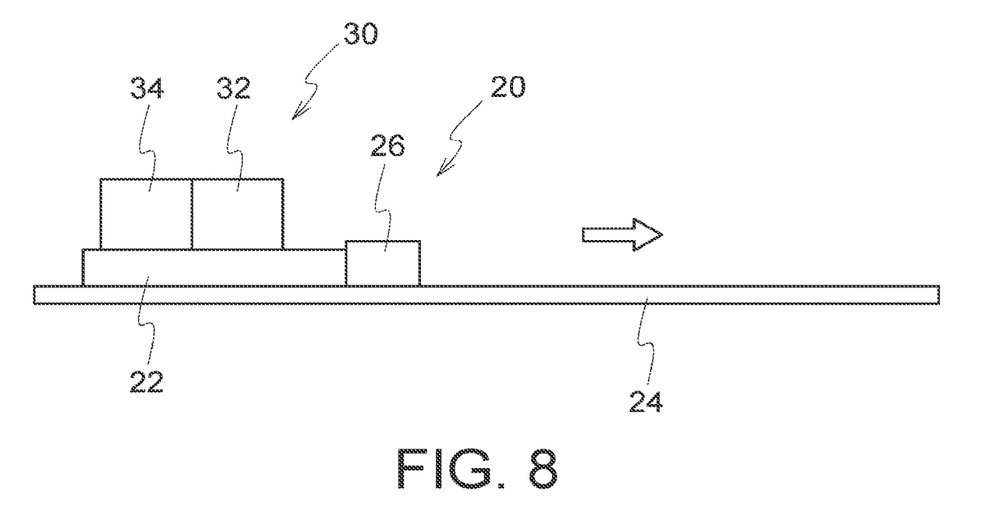
FIG. 8 is a block diagram illustrating an example of the configuration of a radiation quality filter mover included in the X-ray diagnosis apparatus shown in FIG. 7.

FIG. 8 is a block diagram illustrating an example of the configuration of a radiation quality filter mover 20 according to the third embodiment. As shown in FIG. 8, the radiation quality filter 30 of the radiation quality filter mover 20 according to the third embodiment includes a sub-radiation quality filter 32 and a sub-radiation quality filter 34 placed on a support 22 of the radiation quality filter mover 20 located below (in the X-ray emitting direction) of the multifocal X-ray tube 10. The two sub-radiation quality filters 32 and 34 are used to adjust the energy of photons of the X-rays emitted from the multifocal X-ray tube 10, thereby adjusting the radiation quality of the X-rays.

The materials of the sub-radiation quality filter 32 and the sub-radiation quality filter 34 are not particularly limited. However, in the third embodiment, the sub-radiation quality filter 32 and the sub-radiation quality filter 34 are formed of different materials. In other words, the sub-radiation quality filter 32 and the sub-radiation quality filter 34 have different physical characteristics for changing the radiation quality of the X-rays. For example, if the sub-radiation quality filter 32 is formed of rhodium (Rh), the sub-radiation quality filter 34 is formed of a material other than Rh, such as silver (Ag). As a result, the X-rays emitted from each focal point of the multifocal X-ray tube 10 are caused to have different radiation qualities depending on whether they pass through the sub-radiation quality filter 32 or the sub-radiation quality filter 34. Thus, it is possible to use two types of X-rays with different characteristics or different doses.

In FIG. 8, the two sub-radiation quality filters 32 and 34 are joined together and mounted on a single support 22. When the motor of the driving mechanism 26 is driven, the sub-radiation quality filters 32 and 34 move together. The two sub-radiation quality filters 32 and 34, however, are not necessarily mounted on a single support 22 but may be separate from each other.

Figure 9:
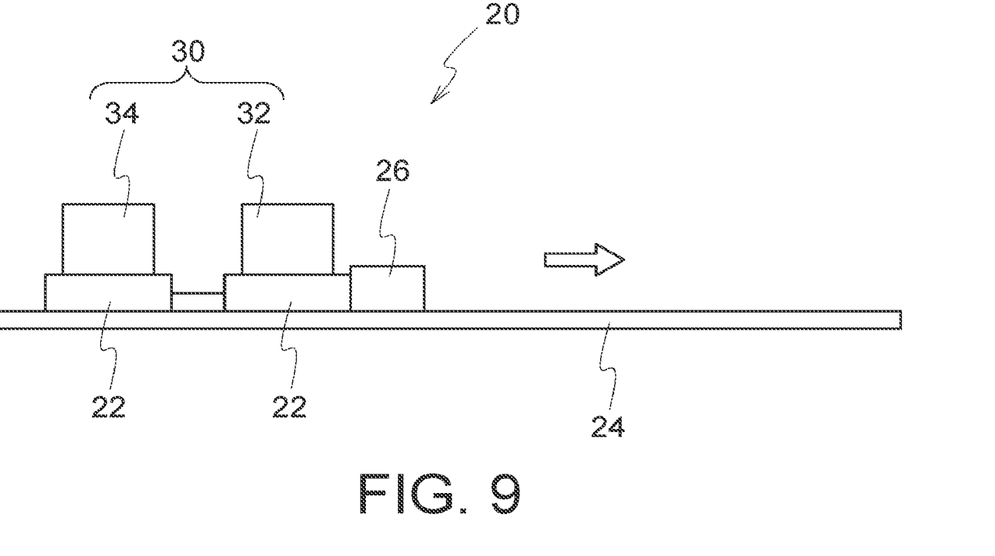
FIG. 9 is a block diagram of a modification of the radiation quality filter mover included in the X-ray diagnosis apparatus shown in FIG. 7.

FIG. 9 is a block diagram illustrating an example of the configuration of a radiation quality filter mover 20 in which the two sub-radiation quality filters 32 and 34 are separated from each other. In the example of FIG. 9, two supports 22 coupled to each other are disposed on a rail 24. The sub-radiation quality filter 32 is mounted on one of the supports 22, and the sub-radiation quality filter 34 is mounted on the other. Since the two supports 22 are coupled to each other, when the motor of the driving mechanism 26 is driven, the sub-radiation quality filters 32 and 34 move together while being separated.

By preparing a plurality of sub-radiation quality filters each having different material characteristics, the X-ray dose may be adjusted depending on the characteristics of the object P. For example, if the right breast of a patient is thicker than the left breast, the X-ray imaging may be performed on the right breast using the sub-radiation quality filter 32 having a higher X-ray transmittance, and the X-ray imaging may be performed on the left breast using the sub-radiation quality filter 34 having a lower X-ray transmittance. In this case, the user needs to input through the user interface 70 which of the sub-radiation quality filters is used for the X-ray imaging. In more detail, when the X-ray imaging of the right breast of the patient is performed, the user places the right breast on the X-ray detector 50, and inputs a command via the user interface 70 to perform the X-ray imaging by means of the sub-radiation quality filter 32 while the X-rays are emitted from the focal points #1 to #5. When the X-ray imaging of the left breast is performed next, the user places the left breast on the X-ray detector 50, and inputs a command via the user interface 70 to perform the X-ray imaging by means of the sub-radiation quality filter 34 while the X-rays are emitted from the focal points #1 to #5.

The X-ray diagnosis apparatus 1 according to the third embodiment is also capable of performing dual-energy imaging. In the dual-energy imaging, a single instruction input by a user initiates an imaging operation for taking images of one object P in a plurality of different energy modes. In more detail, the X-ray imaging while emitting the X-rays from the focal point #1 is performed by using the sub-radiation quality filter 32 and then the X-ray imaging while emitting the X-ray from the focal point #1 is performed by using the sub-radiation quality filter 34. As a result, two X-ray images are taken in different energy modes for the same focal point #1. If this operation is sequentially performed for the focal points #2 to #5, the dual-energy imaging can be implemented.

In addition to a simple X-ray image, a soft tissue image (bone removal image) and a bone tissue image can be obtained by multiplying X-ray images taken at the same position by an appropriate coefficient and by calculating a subtraction. Thereby, for example, it is possible to remove ribs and so on, which are an obstacle shades on the simple X-ray image on chest, and thus it is facilitated to interpret the X-ray image. Although the number of sub-radiation quality filters included in the radiation quality filter 30 is two in the X-ray diagnosis apparatus 1 according to the third embodiment, the number of sub-radiation quality filters included in the radiation quality filter 30 is not limited to two but may be an arbitrary number such as three or four.

The foregoing is the explanation on the difference in configuration between the X-ray diagnosis apparatus 1 according to the third embodiment and the X-ray diagnosis apparatus 1 according to the first embodiment. A process relating to the X-ray imaging performed by the X-ray diagnosis apparatus 1 according to the third embodiment will then be described below.

If one of the sub-radiation quality filters 32 and 34 of the radiation quality filter 30 is used for X-ray imaging, the user inputs a command to select which of the sub-radiation quality filters 32 and 34 is to be used for the X-ray imaging. For example, at step S102 shown in FIG. 3 illustrating the process according to the first embodiment, the user inputs a command for starting the imaging to the X-ray diagnosis apparatus 1 via the user interface 70. At this time, the user may select one of the sub-radiation quality filters 32 and 34 and input a command for using the selected one of the sub-radiation quality filters 32 and 34. If the user selects the sub-radiation quality filter 32, for example, the X-ray diagnosis apparatus 1 uses the sub-radiation quality filter 32 as the radiation quality filter when an X-ray image is taken by the X-rays emitted from the focal points #1 to #5.

Alternatively, the controller 60 of the X-ray diagnosis apparatus 1 may automatically detect the thickness of the object P when the user inputs a command to start X-ray imaging at step S103 shown in FIG. 3, and determine which of the sub-radiation quality filter 32 and the sub-radiation quality filter 34 is used based on the detected thickness of the object P. In this case, for example, a sensor for detecting the distance between the compression plate 40 and the X-ray detector 50 may be provided to calculate the thickness of the object P based on the distance detected by the sensor.

The X-ray imaging operation of the X-ray diagnosis apparatus 1 according to the third embodiment is the same as that of the first embodiment except that one of the sub-radiation quality filters needs to be selected for the X-ray imaging.

Figure 10:
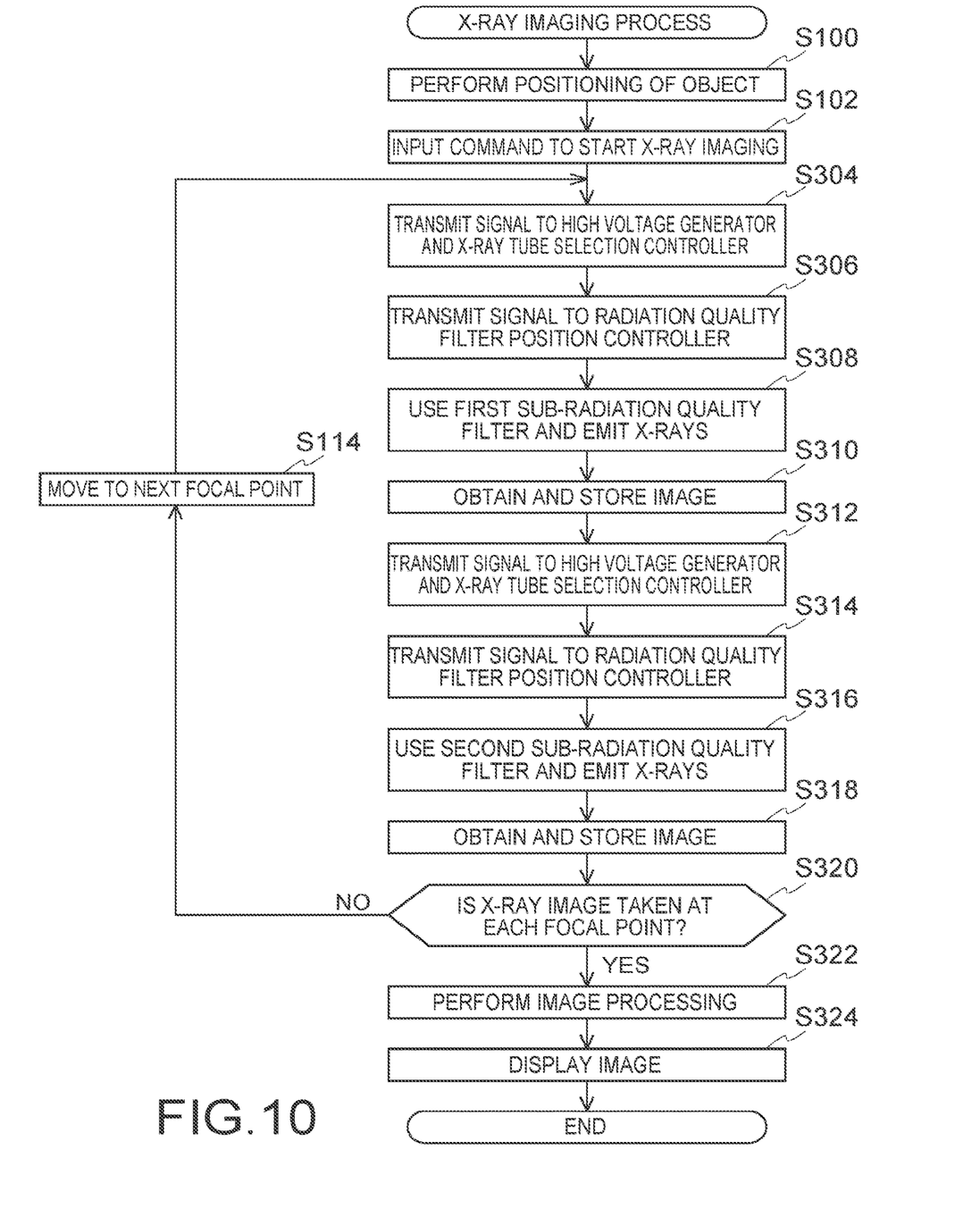
FIG. 10 is a flowchart of an X-ray imaging process performed by the X-ray diagnosis apparatus according to the third embodiment.

If both of the sub-radiation quality filters 32 and 34 are to be used for the X-ray imaging, the X-ray imaging operation of the X-ray diagnosis apparatus 1 is different from that described above. FIG. 10 is a flowchart of the process performed by the X-ray diagnosis apparatus 1 in this case. In the X-ray imaging process shown in FIG. 10, so-called dual energy imaging is performed, in which the sub-radiation quality filter 32 is used as a radiation quality filter and then the sub-radiation quality filter 34 is used as the radiation quality filter in the in X-ray imaging at each of the focal points #1 to #5 of the multifocal X-ray tube 10. A difference between the X-ray imaging process shown in FIG. 10 and that of the first embodiment will be described below.

The steps from the positioning of the object P (step S100) to the input by the user of the start of the imaging (step S102) are performed in the same manner as the first embodiment. After those steps, however, X-ray imaging is first performed by using the sub-radiation quality filter 32, which is a first sub-radiation quality filter, and then X-ray imaging is performed by using the sub-radiation quality filter 34, which is a second sub-radiation quality filter. This is a difference between the third embodiment and the first embodiment. That is, two X-ray imaging operations are performed for one focal point.

Steps S304 to S310 shown in FIG. 10 correspond to steps S104 to S110 of the first embodiment shown in FIG. 3. In step S308, however, the sub-radiation quality filter 32, which is the first sub-radiation quality filter, is moved to the filter position corresponding to the focal point, from which X-rays are emitted, to receive the X-rays. When the sub-radiation quality filter 32 is at the filter position, X-rays are emitted from the focal point of the multifocal X-ray tube 10, the focal point corresponding to the filter position, so that an X-ray image may be obtained by the X-rays having the radiation quality that matches the characteristics of the sub-radiation quality filter 32.

At step S310, the X-ray diagnosis apparatus 1 stores the taken X-ray image in the image storage 110. Thereafter, steps S312 to S318 are performed to take an X-ray image by using the sub-radiation quality filter 34, which is the second sub-radiation quality filter. Steps S312 to S318 also correspond to steps S104 to S110 of the first embodiment shown in FIG. 3. In step S316, however, the second sub-radiation quality filter 34 is moved to the filter position corresponding to the focal point, from which the X-rays are emitted, to receive the X-rays. When the sub-radiation quality filter 34 is at the filter position, X-rays are emitted from the focal point of the multifocal X-ray tube 10, the focal point corresponding to the filter position, so that an X-ray image may be obtained by the X-rays having the radiation quality that matches the characteristics of the sub-radiation quality filter 34.

At step S320, the X-ray diagnosis apparatus 1 determines whether X-ray images are taken by using all of the focal points of the multifocal X-ray tube 10 (step S320). Since the multifocal X-ray tube 10 according to the third embodiment has the five focal points #1 to #5, the X-ray diagnosis apparatus 1 determines whether X-ray imaging is performed two times for each of the focal points #1 to #5.

If the X-ray imaging has not been performed for all of the focal points (No at step S320), the X-ray diagnosis apparatus 1 changes the focal point from which the X-rays are emitted (step S114), and repeats the steps from step S304. Thus, at the next focal point, the X-ray imaging is performed two times.

If the X-ray diagnosis apparatus 1 determines that X-ray imaging has been performed by using all of the focal points (Yes at S320), the X-ray diagnosis apparatus 1 performs image processing based on the X-ray images taken by using the X-rays emitted from each of the focal points of the multifocal X-ray tube 10 (step S322). Specifically, the X-ray diagnosis apparatus 1 reads the X-ray images stored in the image storage 110, and performs regenerating processing based on the X-ray images to produce a single X-ray image. At this time, an X-ray image is produced based on the X-ray images taken by using the sub-radiation quality filter 32, and an X-ray image is produced based on the X-ray images taken by using the sub-radiation quality filter 34. Since the two X-ray images are different in the X-ray intensity and the radiation quality, it is possible to produce a single X-ray image that is finer and more suitable for the diagnosis by synthesizing those two X-rays images.

The X-ray diagnosis apparatus 1 then displays the X-ray image having been subjected to the image processing at step S322 on the image display 130 so as to enable the user to perform the X-ray diagnosis of the object P (step S324). If necessary, the X-ray diagnosis apparatus 1 may store the produced X-ray image in the image storage 110. At this time, not only the single X-ray image that is finally produced but also the two X-ray images produced by using the sub-radiation quality filters 32 and 34 may be displayed and stored. After step S324, the X-ray imaging process is ended.

As described above, since the radiation quality filter 30 included in the X-ray diagnosis apparatus 1 according to the third embodiment includes a plurality of sub-radiation quality filters formed of different materials, X-ray imaging may be performed by using X-rays with different radiation qualities. Therefore, if the object P has a relatively large thickness or density, X-ray imaging may be performed by using the sub-radiation quality filter 32, through which higher energy X-rays, for example, are emitted to the object P. If the object P has a relatively small thickness or density, X-ray imaging may be performed by using the sub-radiation quality filter 34, through which lower energy X-rays are emitted to the object P.

The X-ray diagnosis apparatus 1 according to the third embodiment is capable of generating an X-ray image by using low energy X-rays and an X-ray image by using high energy X-rays in one imaging operation. Thus, a dual energy imaging, for example, can be performed by using the X-ray diagnosis apparatus 1. As a result, an X-ray image that is more accurate and more suitable for the diagnosis may be obtained.

In the descriptions of the first to third embodiments, the X-ray diagnosis apparatus 1 is used for mammography screening in which X-ray imaging of the breast is performed. However, the X-ray diagnosis apparatus 1 may be used not only for mammography screening but also for X-ray imaging of various body parts. For example, the X-ray diagnosis apparatus 1 may be an X-ray imaging apparatus that is capable of producing a long image covering the whole of a leg or the whole of the chest. In such a case, the compression plate 40 may not be provided. By positioning the leg or the chest in front of the multifocal X-ray tube 10, and performing the X-ray imaging by emitting X-rays from the focal points, a long X-ray image may be produced without moving the X-ray tube. The embodiments may be used not only for producing a tomosynthesis image or a long image, but also for an X-ray TV used for barium meal X-ray examination and other general X-ray imaging apparatuses.

In the above descriptions of the first to the third embodiments, the multifocal X-ray tube 10 of the X-ray diagnosis apparatus 1 is of a fixed type. However, the multifocal X-ray tube 10 is not necessarily a fixed type. Thus, the multifocal X-ray tube 10 may be moved so that X-ray imaging may be performed for a broader area of the object P. In this case, the multifocal X-ray tube 10 may be moved after X-ray images are taken by using all of the focal points #1 to #5, and a new set of X-ray images may be taken by using the focal points #1 to #5 again.

The multifocal X-ray tube 10 may be moved linearly or along an arc. If the focal points of the multifocal X-ray tube 10 are linearly arranged, the multifocal X-ray tube 10 may be moved linearly in the direction along which the focal points are arranged. If the focal points of the multifocal X-ray tube 10 are arranged along an arc, the multifocal X-ray tube 10 may be moved along an arc that expends from the arc of the focal points and has the same radius.

In the foregoing, the processors in the controller 60 and the image processor 120 read a program corresponding to each processing function from the storage circuitry. However, the embodiments are not limited to this case. The term "processor" may mean circuitry such as a central processing unit (CPU), a graphics processing unit (GPU), an application specific integrated circuit (ASIC), a programmable logic device such as a simple programmable logic device (SPLD), a complex programmable logic device (CPLD), and a field programmable gate array (FPGA). If the processor is a CPU, for example, the processor reads and executes a program stored in the storage circuitry to perform a processing function. If the processor is an ASIC, the processing function is directly incorporated into the circuitry of the processor as a logic circuit instead of being stored as a program in the storage circuitry. Each processor of the embodiments are not limited to a single circuit but may be formed as a plurality of independent circuits integrated to form a single processor to execute a corresponding processing function. More than one of the elements shown in FIG. 1 may be integrated into a single processor to perform a corresponding processing function.

While certain embodiments have been described, these embodiments have been presented by way of example only, and are not intended to limit the scope of the inventions. The embodiments may be in a variety of other forms. Furthermore, various omissions, substitutions and changes may be made without departing from the spirit of the inventions. The embodiments and their modifications are included in the scope and the subject matter of the invention, and at the same time included in the scope of the claimed inventions and their equivalents.

The invention claimed is:

1. An X-ray diagnosis apparatus comprising:
   an X-ray tube configured to have a plurality of focal points and configured to emit X-rays from each focal point;
   a radiation quality filter configured to change radiation quality of the X-rays emitted from each of the focal points; and
   a mover configured to move the radiation quality filter in a direction along which the focal points are aligned,
   wherein the radiation quality filter is configured to change the radiation quality by adjusting energy of photons of the X-rays emitted from each of the focal points when the X-rays pass through the radiation quality filter.

2. The X-ray diagnosis apparatus according to claim 1, further comprising a controller configured to control the mover so as to position the radiation quality filter at a filter position corresponding to each of the focal points.

3. The X-ray diagnosis apparatus according to claim 1, wherein the mover comprises:
   a guider configured to guide the radiation quality filter in the direction along which the focal points are aligned; and
   a support configured to support the radiation quality filter and configured to be moved while being guided by the guider.

4. The X-ray diagnosis apparatus according to claim 1, wherein the radiation quality filter has an area corresponding to an irradiation field irradiated with the X-rays emitted from each of the focal points.

5. An X-ray diagnosis apparatus, comprising:
   an X-ray tube configured to have a plurality of focal points and configured to emit X-rays from each focal point;
   a radiation quality filter configured to change radiation quality of the X-rays emitted from each of the focal points;
   a mover configured to move the radiation quality filter in a direction along which the focal points are aligned; and
   a controller configured to control the mover so as to position the radiation quality filter at a filter position corresponding to each of the focal points, wherein
   the radiation quality filter includes a plurality of sub-radiation quality filters each being formed of a different material; and
   the mover moves the radiation quality filter including the sub-radiation quality filters.

6. The X-ray diagnosis apparatus according to claim 5, wherein:
   the controller controls the mover so that each of the sub-radiation quality filters is positioned at the filter position; and
   when each of the sub-radiation quality filters are positioned at the filter position, the X-ray tube emits the X-rays from one of the focal points corresponding to the filter position, so that a plurality of X-ray images are formed with X-rays having different radiation qualities.

7. The X-ray diagnosis apparatus according to claim 5, wherein the sub-radiation quality filters are joined together and moves together.

8. The X-ray diagnosis apparatus according to claim 5, wherein the sub-radiation quality filters are separated from each other and move together while being separated.

9. The X-ray diagnosis apparatus according to claim 1, wherein the X-ray diagnosis apparatus is one of a mammography, an X-ray apparatus capable of taking a tomosynthesis image, an X-ray apparatus capable of taking a long image, an X-ray TV and an X-ray apparatus for other general X-ray imaging.

10. The X-ray diagnosis apparatus according to claim 1, wherein the focal points of the X-ray tube are arranged linearly or along an arc.

11. The X-ray diagnosis apparatus according to claim 1, wherein, after X-ray images are taken by emitting the X-rays from the focal points, the X-ray tube is moved and then a new set of X-ray images are taken by emitting the X-rays from the focal points again.

12. The X-ray diagnosis apparatus according to claim 2, wherein when the X-rays are emitted from one of the focal points, the controller controls the mover so that the radiation quality filter is stopped and positioned at the filter position corresponding to the one of the focal points.

13. The X-ray diagnosis apparatus according to claim 2, wherein when the X-rays are emitted from one of the focal points, the controller controls the mover so that the radiation quality filter is not stopped but positioned at the filter position corresponding to the one of the focal points.

14. The X-ray diagnosis apparatus according to claim 1, wherein the radiation quality filter is formed of at least one of molybdenum, rhodium, and silver.

* * * * *